United States Patent [19]

Böhner et al.

[11] Patent Number: 4,549,898
[45] Date of Patent: Oct. 29, 1985

[54] N-HETEROCYCLOSULFONYL-N'-PYRIMIDINYLUREAS AND N-HETEROCYCLOSULFONYL-N'-TRIAZINYLUREAS

[75] Inventors: Beat Böhner, Binningen; Werner Föry, Basel; Karl Gass, Magden; Willy Meyer, Riehen, all of Switzerland

[73] Assignee: Ciba-Geigy Corporation, Ardsley, N.Y.

[21] Appl. No.: 501,459

[22] Filed: Jun. 6, 1983

[30] Foreign Application Priority Data

Jun. 14, 1982 [CH] Switzerland .................... 3671/82

[51] Int. Cl.⁴ ................ C07D 409/12; C07D 407/12; C07D 401/12; A01N 47/36
[52] U.S. Cl. .................................... 71/90; 71/92; 71/93; 544/212; 544/320
[58] Field of Search .................... 544/320; 71/90, 92

[56] References Cited

U.S. PATENT DOCUMENTS 4,214,890  7/1980  Levitt ..................................... 71/90
4,368,067  1/1983  Budzinski .............................. 71/92

FOREIGN PATENT DOCUMENTS 1114819 12/1981 Canada .................................. 544/320
0013480  7/1980 European Pat. Off. ............ 544/320
0030142  6/1981 European Pat. Off. ............ 544/320
0039239 11/1981 European Pat. Off. ............ 544/320
  44807  1/1982 European Pat. Off. ............ 544/211
0070804  1/1983 European Pat. Off. ............ 544/320
2715786 10/1977 Fed. Rep. of Germany ...... 544/320

Primary Examiner—Robert Gerstl
Attorney, Agent, or Firm—Edward McC. Roberts; Bruce M. Collins

[57] ABSTRACT

N-heterocyclosulfonyl-N'-pyrimidinylureas and N-heterocyclosulfonyl-N'-triazinylureas of the general formula I

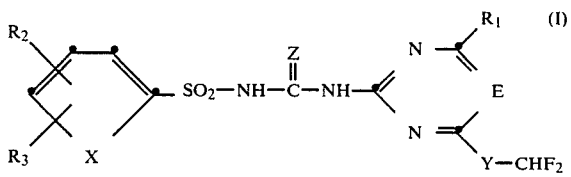

wherein X is oxygen, sulfur,

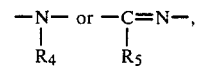

Y is oxygen or sulfur, Z is oxygen or sulfur, E is nitrogen or —CH=, $R_1$ is hydrogen, $C_1$-$C_4$alkyl, $C_1$-$C_4$haloalkyl, $C_1$-$C_4$haloalkoxy, $C_1$-$C_4$alkoxy, halogen, $C_1$-$C_4$alkylthio, —NR$_6$R$_7$ or alkoxyalkyl containing not more than 4 carbon atoms, $R_2$ is hydrogen, $C_1$-$C_3$alkyl, $C_1$-$C_3$ haloalkyl, halogen, nitro, $C_1$-$C_3$alkoxy,

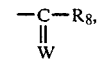

—SO$_2$—NR$_6$R$_7$, —SO$_n$—C$_1$-C$_3$alkyl or —CO—R$_9$, $R_3$ is hydrogen, halogen, $C_1$-$C_3$alkyl, methoxy, nitro or trifluoromethyl, $R_4$ is hydrogen, $C_1$-$C_4$alkyl, $C_1$-$C_4$cyanoalkyl, $C_3$-$C_6$cycloalkyl, benzyl, —CO—$C_1$-$C_4$alkoxy, —CO—NR$_6$R$_7$ or —CO—$C_1$-$C_4$alkyl which is unsubstituted or substituted by 1 to 3 halogen atoms, $R_5$ is hydrogen, nitro, fluorine, chlorine, bromine, methyl, trifluoromethyl, —SO$_n$—C$_1$-C$_3$alkyl, —CO—$C_1$-$C_4$alkoxy or $C_1$-$C_3$alkoxy, $R_6$ is hydrogen, $C_1$-$C_6$alkyl, $C_1$-$C_4$cyanoalkyl, methoxy or ethoxy, $R_7$ is hydrogen, $C_1$-$C_6$alkyl or $C_3$-$C_6$alkenyl, or $R_6$ and $R_7$, together with the nitrogen atom to which they are attached, form a 5- or 6-membered saturated heterocyclic ring which may contain an oxygen or a sulfur atom as ring member, $R_8$ is hydrogen, $C_1$-$C_6$alkyl, $C_1$-$C_4$haloalkyl, $C_3$-$C_6$cycloalkyl, $C_4$-$C_hd 7$cycloalkylalkyl or alkoxyalkyl containing not more than 4 carbon atoms, $R_9$ is $C_1$-$C_6$alkoxy, $C_3$-$C_6$alkenyloxy, $C_3$-$C_6$alkynyloxy, $C_2$-$C_6$haloalkoxy, $C_1$-$C_4$cyanoalkoxy, $C_1$-$C_6$alkylthio, $C_3$-$C_6$alkenylthio, $C_3$-$C_6$alkynylthio, $C_5$-$C_6$cycloalkoxy, $C_4$-$C_7$cycloalkylalkoxy, —NR$_6$R$_7$ or alkoxyalkoxy containing not more than 6 carbon atoms, W is oxygen or =N—O—R$_{10}$, wherein R$_{10}$ is hydrogen, $C_1$-$C_6$alkyl or $C_3$-$C_6$alkenyl, and n is a value from 0 to 2 and the salts of these compounds with amines, alkali metal bases or alkaline earth metal bases or with quaternary ammonium bases, have good preemergence and postemergence selective herbicidal and growth regulating properties.

17 Claims, No Drawings

N-HETEROCYCLOSULFONYL-N'-PYRIMIDINYLUREAS AND N-HETEROCYCLOSULFONYL-N'-TRIAZINYLUREAS

The present invention relates to novel N-heterocyclosulfonyl-N'-pyrimidinylureas and N-heterocyclosulfonyl-N-triazinylureas with herbicidal and growth regulating properties, to the preparation thereof, to compositions containing these novel compounds, and to the use thereof for controlling weeds, in particular selectively, in crops of useful plants, or for regulating and inhibiting plant growth.

The heterocyclosulfonyl-N'-pyrimidinylureas and N-heterocyclosulfonyl-N-triazinylureas, and the salts thereof, have the general formula I

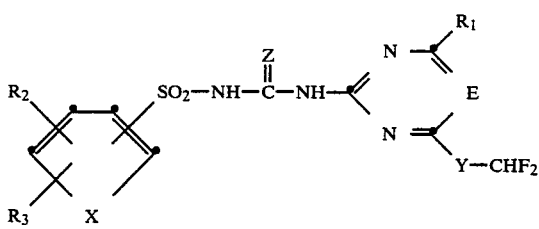

wherein

X is oxygen, sulfur,

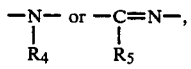

Y is oxygen or sulfur,
Z is oxygen or sulfur,
E is nitrogen or —CH=,
$R_1$ is hydrogen, $C_1$-$C_4$alkyl, $C_1$-$C_4$haloalkyl, $C_1$-$C_4$haloalkoxy, $C_1$-$C_4$alkoxy, halogen, $C_1$-$C_4$alkylthio, —$NR_6R_7$ or alkoxyalkyl containing not more than 4 carbon atoms,
$R_2$ is hydrogen,
$C_1$-$C_3$alkyl, $C_1$-$C_3$ haloalkyl, halogen, nitro, $C_1$-$C_3$alkoxy,

—$SO_2$—$NR_6R_7$, —$SO_n$—$C_1$-$C_3$alkyl or —CO—$R_9$,
$R_3$ is hydrogen, halogen, $C_1$-$C_3$alkyl, methoxy, nitro or trifluoromethyl,
$R_4$ is hydrogen, $C_1$-$C_4$alkyl, $C_1$-$C_4$cyanoalkyl, $C_3$-$C_6$-cycloalkyl, benzyl, —CO—$C_1$-$C_4$alkoxy, —CO—$NR_6R_7$ or —CO—$C_1$-$C_4$alkyl which is unsubstituted or substituted by 1 to 3 halogen atoms,
$R_5$ is hydrogen, nitro, fluorine, chlorine, bromine, methyl, trifluoromethyl, —$SO_n$—$C_1$-$C_3$alkyl, —CO—$C_1$-$C_4$alkoxy or $C_1$-$C_3$alkoxy,
$R_6$ is hydrogen, $C_1$-$C_6$alkyl, $C_1$-$C_4$-cyanoalkyl, methoxy or ethoxy,
$R_7$ is hydrogen, $C_1$-$C_6$alkyl or $C_3$-$C_6$alkenyl, or
$R_6$ and $R_7$, together with the nitrogen atom to which they are attached, form a 5- or 6-membered saturated heterocyclic ring which may contain an oxygen or a sulfur atom as ring member,
$R_8$ is hydrogen, $C_1$-$C_6$alkyl, $C_1$-$C_4$haloalkyl, $C_3$-$C_6$cycloalkyl, $C_4$-$C_7$cycloalkylalkyl or alkoxyalkyl containing not more than 4 carbon atoms,
$R_9$ is $C_1$-$C_6$alkoxy, $C_3$-$C_6$alkenyloxy, $C_3$-$C_6$alkynyloxy, $C_2$-$C_6$haloalkoxy, $C_1$-$C_4$cyanoalkoxy, $C_1$-$C_6$alkylthio, $C_3$-$C_6$alkenylthio, $C_3$-$C_6$alkynylthio, $C_5$-$C_6$cycloalkoxy, $C_4$-$C_7$ cycloalkylalkoxy, —$NR_6R_7$ or alkoxyalkoxy containing not more than 6 carbon atoms,
W is oxygen or =N—O—$R_{10}$, wherein $R_{10}$ is hydrogen, $C_1$-$C_6$alkyl or $C_3$-$C_6$alkenyl, and
n is a value from 0 to 2.

Herbicidally active ureas, triazines and pyrimidines are generally known in the art. Arylsulfonyl-heterocylyureas with herbicidal and plant growth-regulating action are described e.g. in European patent application Nos. 13480, 30142 or 39239, or in German Offenlegungsschrift No. 2 715 786.

In the above definitions, alkyl denotes straight-chain or branched alkyl, e.g. methyl, ethyl, n-propyl, isopropyl, the butyl, pentyl or hexyl isomers.

Alkoxy denotes methoxy, ethoxy, n-propoxy, isopropoxy, the four butoxy isomers, n-amyloxy, isoamyloxy, 2-amyloxy or 3-amyloxy, with methoxy, ethoxy, or isopropoxy being preferred.

Alkylthio is e.g. methylthio, ethylthio, n-propylthio, isopropylthio and n-butylthio, with methylthio and ethylthio being preferred.

Cycloalkyl within the scope of formula I denotes cyclopropyl, cyclobutyl, cyclopentyl and cyclohexyl.

Typical examples of cycloalkylalkyl are cyclopropylmethyl, cyclopropylethyl, cyclopropylpropyl, cyclobutylmethyl, cyclobutylethyl, cyclopentylmethyl, cyclopentylethyl and cyclohexylmethyl. Preferred identities are cyclopentylmethyl, cyclohexylmethyl and cyclopropylmethyl.

Preferred cyanoalkyl radicals are in general cyanomethyl, cyanoethyl and cyanopropyl.

Preferred heterocyclic rings which can be formed by $R_6$ and $R_7$ together with the nitrogen atom to which they are attached are pyrrolidine, piperidine, morpholine or thiomorpholine.

Alkoxyalkyl radicals are preferably methoxymethyl, methoxyethyl, ethoxymethyl and ethoxyethyl.

Heterocyclic rings X which are bound through the sulfonyl group comprise furane, thiophene, pyrrole and pyridine.

Alkenyl radicals are e.g. vinyl, allyl, isoprenyl, propen-1-yl, buten-1-yl, buten-2-yl, buten-3-yl, isobuten-1-yl, isobuten-2-yl, penten-1-yl, penten-2-yl, penten-3-yl, penten-4-yl and the hexenyl isomers, with vinyl, allyl and penten-4-yl being the preferred identities.

Alkylsulfinyl is e.g. methylsulfinyl, ethylsulfinyl, n-propylsulfinyl and n-butylsulfinyl. Preferred identities are methylsulfinyl and ethylsulfinyl.

Alkylsulfonyl is e.g. methylsulfonyl, ethylsulfonyl or n-propylsulfonyl. Preferred identities are methylsulfonyl and ethylsulfonyl.

Halogen in the above definitons, as well as moiety of haloalkyl, haloalkoxy and haloalkylthio, is fluorine, chlorine and bromine, with fluorine and chlorine being preferred.

Alkynyl radicals in the above definitons are generally propargyl, butyn-2-yl, butyn-3-yl, as well as pentynyl isomers. Preferably, however, alkynyl is propargyl or butyn-2- or 3-yl.

The invention also comprises the salts which the compounds of formula I are able to form with amines alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which (a) Z is oxygen, or
(b) Y is oxygen or
(c) X is sulfur, —NR$_4$— or —CR$_5$=N— or
(d) E is the methine bridge —CH= or
(e) R$_1$ is chlorine, dimethylamino, trifluoromethyl, fluoromethyl, methoxy, ethoxy, difluoromethoxy, methyl or ethyl, or
(f) R$_3$ is hydrogen or
(g) the radical R$_2$ is vicinal to the sulfonyl group.

Preferred compounds of subgroup (g) are those in which R$_2$ is hydrogen, fluorine, chlorine, NO$_2$, C$_1$-C$_3$ alkoxy, acetyl, —COOCH$_2$—CH=CH$_2$, —COOCH$_2$—CH$_2$—OCH$_3$, —COOCH$_2$—C≡CH, —SO$_2$—N(CH$_3$)$_2$, —SO$_2$CH$_3$ or —CO—C$_1$-C$_4$alkoxy.

A further preferred subgroup comprises compounds of formula I, wherein Y and Z are oxygen, E is the methine bridge, R$_1$ is chlorine, dimethylamino, trifluoromethyl, fluoromethyl, methoxy, difluoromethoxy, ethoxy, methyl or ethyl, R$_2$ is vicinal to the sulfonyl group and is hydrogen, fluorine, chlorine, C$_1$-C$_3$alkoxy, acetyl, NO$_2$, —SO$_2$—CH$_3$, —COOCH$_2$—CH=CH$_2$, —COOCH$_2$13 CH$_2$—OCH$_3$, —COOCH$_2$—C≡CH, —SO$_2$—N(CH$_3$)$_2$ or —CO—C$_1$-C$_4$alkoxy, and R$_3$ is hydrogen.

The most preferred subgroups of compounds of formula I are (1) compounds wherein X is a sulfur atom, Y and Z are oxygen, E is the methine bridge, R$_1$ is chlorine, dimethylamino, trifluoromethyl, fluoromethyl, methoxy, ethoxy, difluoromethoxy, methyl or ethyl, R$_2$ is vicinal to the sulfonyl group and is hydrogen, fluorine, chlorine, C$_1$-C$_3$alkoxy, acetyl, —SO$_2$—CH$_3$, NO$_2$, —COOCH$_2$—CH=CH$_2$, —COOCH$_2$—CH$_2$—OCH$_3$, —COOCH$_2$—C≡CH, —SO$_2$—N(CH$_3$)$_2$ or —CO—C$_1$-C$_4$alkoxy, and R$_3$ is hydrogen;

(2) compounds wherein X is —NR$_4$—, Y and Z are oxygen, E is the methine bridge, R$_1$ is chlorine, dimethylamino, trifluoromethyl, fluoromethyl, methoxy, difluoromethoxy, methyl or ethyl, R$_2$ is vicinal to the sulfonyl group and is hydrogen, fluorine, chlorine, C$_1$-C$_3$-alkoxy, acetyl, NO$_2$, —SO$_2$—CH$_3$, —COOCH$_2$—CH=CH$_2$, —COOCH$_2$CH$_2$OCH$_3$, —COOCH$_2$—C≡CH, —SO$_2$—N(CH$_3$)$_2$ or —CO—C$_1$-C$_4$alkoxy, and R$_3$ is hydrogen;

(3) compounds wherein X is —CR$_5$=N—, Y and Z are oxygen, E is the methine bridge, R$_1$ is chlorine, dimethylamino, trifluoromethyl, fluoromethyl, methoxy, ethoxy, difluoromethoxy, methyl or ethyl, R$_2$ is vicinal to the sulfonyl group and is hydrogen, fluorine, chlorine, NO$_2$, C$_1$-C$_3$alkoxy, acetyl, —SO$_2$—CH$_3$, —COOCH$_2$—CH=CH$_2$, —COOCH$_2$—CH$_2$—OCH$_3$, —COOCH$_2$—C≡CH, —SO$_2$—N(CH$_3$)$_2$ or —CO—C$_1$-C$_4$alkoxy, and R$_3$ is hydrogen.

Preferred individual compounds are:

N'-(2-methoxycarbonyl-3-thienylsulfonyl)-N'-(4-difluoromethoxy-6-methylpyrimidin-2-yl)urea,
N'-(4-methoxycarbonyl-3-thienylsulfonyl)-N'-(4-difluoromethoxy-6-methoxypyrimidin-2-yl)urea,
N'-(4-methoxycarbonyl-3-thienylsulfonyl)-N'-(4-difluoromethoxy-6-methylpyrimidin-2-yl)urea,
N-(2-chloro-3-pyridylsulfonyl)-N'-(4-difluoromethoxy-6-methylpyrimidin-2-yl)urea,
N-(2-pyridinylsulfonyl)-N'-(4-difluoromethoxy-6-methylpyrimidin-2-yl)urea,
N-(2-pyrrolylsulfonyl)-N'-(4-difluoromethoxy-6-methylpyrimidin-2-yl)urea and
N-(3-pyrrolylsulfonyl)-N'-(4-difluoromethoxy-6-methylpyrimidin-2-yl)urea.

The process for obtaining the compounds of formula I is carried out in an inert organic solvent.

In a first process, the compounds of the formula I are obtained by reacting a heterocyclosulfonamide of the formula II

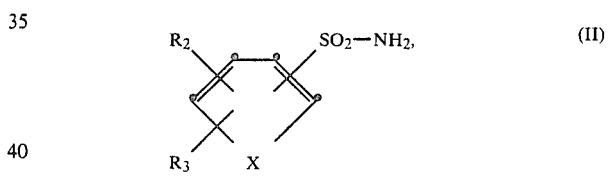

wherein X, R$_2$ and R$_3$ are as defined for formula I, with a N-pyrimidinylcarbamate or N-triazinylcarbamate of the formula III

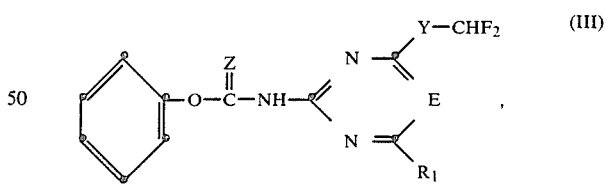

wherein E, R$_1$, Y and Z are as defined for formula I, in the presence of a base.

In a second process, compound of formula I are obtained by reacting a heterocyclosulfonylisocyanate or heterocyclosulfonylisothiocyanate of the formula IV

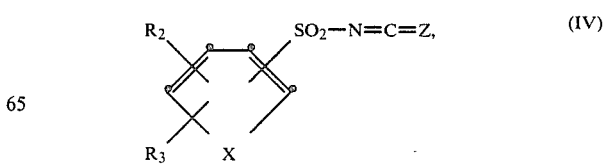

wherein R$_2$, R$_3$, X and Z are as defined for formula I, with an aminopyrimidine or aminotriazine of the formula V

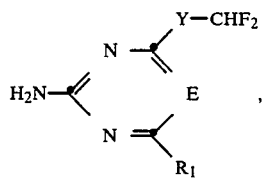

wherein E, R$_1$ and Y are as defined for formula I, optionally in the presence of a base.

In a further process, the compounds of formula I are obtained by reacting a heterocyclosulfonamide of the formula II above with an isocyanate or isothiocyanate of the formula VI

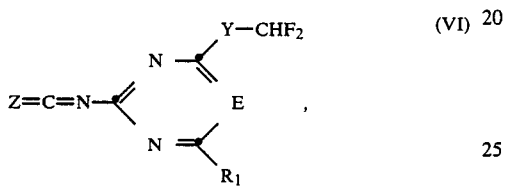

wherein E, R$_1$, Y and Z are as defined for formula I, optionally in the presence of a base.

Finally, the compounds of formula I can also be obtained by reacting a N-heterocyclosulfonylcarbamate of the formula VII

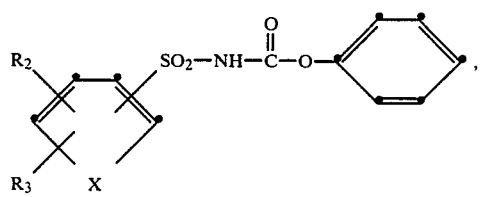

wherein R$_2$, R$_3$ and X are as defined for formula I, with an aminopyrimidine or aminotriazine of the formula V above.

If desired, the ureas of formula I can be converted into addition salts with amines, alkali metal hydroxides or alkaline earth metal hydroxides, or with quaternary ammonium bases. This conversion is carried out e.g. by reacting the compounds of formula I with the equimolar amount of a base and removing the solvent by evaporation.

It is convenient to carry out these reactions for obtaining compounds of formula I in aprotic, inert organic solvents such as methylene chloride, tetrahydrofuran, acetonitrile, dioxan or toluene.

The reaction temperatures are preferably in the range from $-20°$ to $+120°$ C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The bases employed may be both organic bases such as amines, e.g. triethylamine, quinuclidine, pyridine etc., and inorganic bases, e.g. hydrides such as sodium hydride or calcium hydride, hydroxides such as sodium hydroxide or potassium hydroxide, or bicarbonates such as potassium bicarbonate or sodium bicarbonate.

The final products can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

The compounds of formula I are stable compounds, and no protective measures are required for handling them.

The intermediates of the formulae II, IV and VII are known or they can be prepared by known methods.

Compounds of formula V are obtained in accordance with European patent application No. 70 804 by reacting an aminopyridine or aminotriazine of the formula VIII

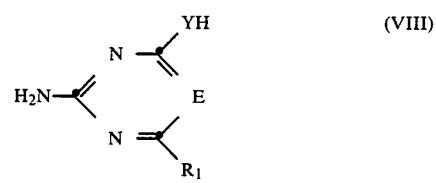

wherein R$_1$, Y and E are as defined for formula I, with difluorochloromethane or difluorobromomethane, in the presence of a base.

The process for the preparation of compounds of formula V is conveniently carried out in an inert polar solvent or mixture of solvents. Suitable solvents are ethers such as dioxan, tetrahydrofuran, ethylene glycol dimethyl ether, diethylene glycol dimethyl ether; alcohols such as methanol or ethanol; ketones such as acetone or ethyl methyl ketone; dimethylformamide; acetonitrile or dimethylsulfoxide. Particularly suitable bases are: sodium hydride and calcium hydride, potassium hydroxide and sodium hydroxide, potassium carbonate and sodium bicarbonate. In suitable cases, the base may be added in the form of an aqueous solution.

The starting materials of the formula VIII are known or they may be obtained by methods similar to known ones. The intermediates of the formulae III and VI are obtained from the intermediates of formula V by methods corresponding to known ones.

When used in low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used in very low rates of application.

The compounds of formula I have in addition pronounced growth-regulating, especially growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whilst vegetative growth is inhibited.

Further, the compounds of formula I are suitable for preventing stored potatoes from seeding. During winter storage, potatoes often develop sprouts which result in shrinkage, weight loss, and rot.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipides.

Non-ionic surfactants are preferably polyglycol ether derivatives of aliphatic of cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol units.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acids esters of polyoxyethylene sorbitan and polyoxyethylene sorbitan trioleate are also suitable non-ionic surfactants.

Cationic surfactants are preferably quaternary ammonium salts which contain, an N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979, and Sisley and Wood, "Encyclopedia of Surface Active Agents", Chemical Publishing Co., Inc. New York, 1964.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 10 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001%. The rates of application are normally from 0.01 to 10 kg a.i./ha, preferably from 0.025 to 5 kg a.i./ha.

PREPARATORY EXAMPLES

EXAMPLE 1

N-(2-Methoxycarbonyl-3-thienylsulfonyl)-N'-(4-difluoromethoxy-6-methylpyrimidin-2-yl)urea A solution of 6.2 g of 2-methoxycarbonyl-3-thienylsulfonylisocyanate in 50 ml of absolute tetrahydrofuran is stirred dropwise into a solution of 4.4 g of 2-amino-4-difluoromethoxy-6-methylpyrimidine in 80 ml of absolute tetrahydrofuran. During the course of this addition, the temperature of the reaction mixture rises from 20° to 26° C. After it has been stirred for another hour, the raction mixture is filtered and the filtrate is concentrated. The residue is crystallised from ethyl acetate, affording 5.3 g (50%) of N-(2-methoxycarbonyl-3-thienylsulfonyl)-N'-(4-difluoromethoxy-6-methylpyrimidin-2-yl)urea (compound 2.1) with a melting point of 178°–179° C.

EXAMPLE 2

N-(2-Chloro-3-pyridinylsulfonyl)-N'-(4-difluoromethoxy-6-methylpyrimidin-2-yl)urea To a mixture of 0.652 g of 2-chloro-3-pyridinylsulfonamide and 0.55 ml of 1,8-diazabicyclo[5.4.0]undec-7-ene in 10 ml of absolute dioxan is added, at 25° C., 1 g of N-(4-difluoromethoxy-6-methylpyrimidin-2-yl)phenylcarbamate. The reaction mixture is stirred for another 2 hours at the same temperature and then concentrated. The residue is taken up in ice/water and neutralised with 1.86 ml of 2N hydrochloric acid. The precipitate is isolated, washed with water and dreid, affording 1.2 g (90%) of N-(2-chloro-3-pyridinylsulfonyl)-N'-(4-difluoromethoxy-6-methylpyrimidin-2-yl)urea (compound 1.15) with a melting point of 161°–162° C.

EXAMPLE 3

N-(2-Pyridinylsulfonyl)-N'-(4-difluoromethoxy-6-methylpyrimidin-2-yl)-urea

To a solution of 0.52 g of 2-pyridinylsulfonamide and 0.55 g of 1,8-diazabicyclo[5.4.0]undec-7-ene in 10 ml of absolute dioxan is added 1 g of N-(4-difluoromethoxy-6-methylpyrimidin-2-yl)-phenylcarbamate. The reaction mixture is stirred for 6 hours at 20°–25° C., then taken up in water and acidified with 2N hydrochloric acid. The precipitate is isolated, washed with water and recrystallised from a mixture of acetone/ether, affording 0.5 g (42.4%) of N-(2-pyridinylsulfonyl)-N'-(4-difluoromethoxy-6-methylpyrimidin-2-yl)urea (compound 1.1) with a melting point of 150°–151° C.

EXAMPLE 4

N-Pyrrolylsulfonyl-N'-(4-difluoromethoxy-6-methylpyrimidin-2-yl)urea 5.7 g of chlorosulfonylisocyanate are added dropwise at 0°–5° C. to a solution of 7 g of 2-amino-4-difluoromethoxy-6-methylpyrimidine in 100 ml of absolute tetrahydrofuran. The yellowish solution is stirred for 10 minutes at 0° C., then 5.6 ml of pyrrole are added and the reaction mixture is stirred for 17 hours at 20°–25° C. The solvent is evaporated off and the residue is taken up in a mixture of 25 ml of methanol, 50 ml of water and 3.2 g of sodium hydroxide. The solution is shaken vigorously for 10 minutes, washed with two 50 ml portions of methylene chloride and acidified with glacial acetic acid. The acid aqueous solution is then extracted with ethyl acetate. The organic extracts are dried over magnesium sulfate and concentrated to give a 1:1 mixture of two isomers in 20% yield. This mixture of isomers is chromatographed over silica gel with a 4:1 mixture of petroleum ether/ethyl acetate, affording N-(2-pyrrolylsulfonyl)-N'-4-difluoromethoxy-6-methylpyrimidin-2-yl)urea with a melting point of 189° C. (compound 4.1) and N-(3-pyrrolylsulfonyl)-N'-(4-difluoromethoxy-6-methylpyrimidin-2-yl)urea with a melting point of 173°–174° C. (compound 4.8).

The compounds of formula I listed in the following Tables 1 to 4 are prepared in corresponding manner.

TABLE 1

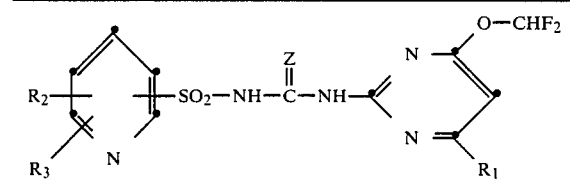

| Compound | $R_1$ | $R_2$ | Position of the sulfonyl group | $R_3$ | Z | m.p. [°C.] |
|---|---|---|---|---|---|---|
| 1.1 | $CH_3$ | H | 2 | H | O | 150–151 |
| 1.2 | $OCH_3$ | H | 2 | H | O | |
| 1.3 | Cl | H | 2 | H | O | |
| 1.4 | $-N(CH_3)_2$ | H | 2 | H | O | |

TABLE 1-continued

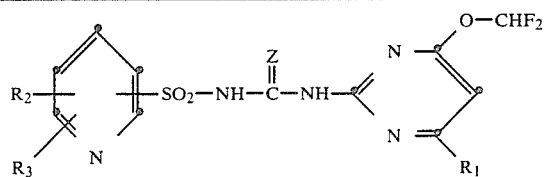

| Compound | R₁ | R₂ | Position of the sulfonyl group | R₃ | Z | m.p. [°C] |
|---|---|---|---|---|---|---|
| 1.5 | C₂H₅ | H | 2 | H | O | |
| 1.6 | CF₃ | H | 2 | H | O | |
| 1.7 | —OCHF₂ | H | 2 | H | O | |
| 1.8 | CH₃ | H | 3 | H | O | |
| 1.9 | OCH₃ | H | 3 | H | O | |
| 1.10 | Cl | H | 3 | H | O | |
| 1.11 | —N(CH₃)₂ | H | 3 | H | O | |
| 1.12 | C₂H₅ | H | 3 | H | O | |
| 1.13 | CF₃ | H | 3 | H | O | |
| 1.14 | —OCHF₂ | H | 3 | H | O | |
| 1.15 | CH₃ | 2-Cl | 3 | H | O | 161–162 |
| 1.16 | OCH₃ | 2-Cl | 3 | H | O | |
| 1.17 | Cl | 2-Cl | 3 | H | O | |
| 1.18 | —N(CH₃)₂ | 2-Cl | 3 | H | O | |
| 1.19 | C₂H₅ | 2-Cl | 3 | H | O | |
| 1.20 | CF₃ | 2-Cl | 3 | H | O | |
| 1.21 | —OCHF₂ | 2-Cl | 3 | H | O | |
| 1.22 | CH₃ | 2-COOCH₃ | 3 | H | O | |
| 1.23 | OCH₃ | 2-COOCH₃ | 3 | H | O | |
| 1.24 | Cl | 2-COOCH₃ | 3 | H | O | |
| 1.25 | —N(CH₃)₂ | 2-COOCH₃ | 3 | H | O | |
| 1.26 | C₂H₅ | 2-COOCH₃ | 3 | H | O | |
| 1.27 | CF₃ | 2-COOCH₃ | 3 | H | O | |
| 1.28 | —OCHF₂ | 2-COOCH₃ | 3 | H | O | |
| 1.29 | CH₃ | 2-SO₂—CH₃ | 3 | H | O | 184 (decomp.) |
| 1.30 | OCH₃ | 2-SO₂—CH₃ | 3 | H | O | |
| 1.31 | Cl | 2-SO₂—CH₃ | 3 | H | O | |
| 1.32 | —N(CH₃)₂ | 2-SO₂—CH₃ | 3 | H | O | |
| 1.33 | C₂H₅ | 2-SO₂—CH₃ | 3 | H | O | |
| 1.34 | CF₃ | 2-SO₂—CH₃ | 3 | H | O | |
| 1.35 | —OCHF₂ | 2-SO₂—CH₃ | 3 | H | O | |
| 1.36 | CH₃ | 2-F | 3 | H | O | |
| 1.37 | OCH₃ | 2-F | 3 | H | O | |
| 1.38 | Cl | 2-F | 3 | H | O | |
| 1.39 | —N(CH₃)₂ | 2-F | 3 | H | O | |
| 1.40 | C₂H₅ | 2-F | 3 | H | O | |
| 1.41 | CF₃ | 2-F | 3 | H | O | |
| 1.42 | —OCHF₂ | 2-F | 3 | H | O | |
| 1.43 | CH₃ | 3-Cl | 3 | H | O | |
| 1.44 | OCH₃ | 3-Cl | 2 | H | O | |
| 1.45 | Cl | 3-Cl | 2 | H | O | |
| 1.46 | —N(CH₃)₂ | 3-Cl | 2 | H | O | |
| 1.47 | C₂H₅ | 3-Cl | 2 | H | O | |
| 1.48 | CF₃ | 3-Cl | 2 | H | O | |
| 1.49 | —OCHF₂ | 3-Cl | 2 | H | O | |
| 1.50 | CH₃ | 3-OCH₃ | 2 | H | O | 161 (decomp.) |
| 1.51 | OCH₃ | 3-OCH₃ | 2 | H | O | |
| 1.52 | Cl | 3-OCH₃ | 2 | H | O | |
| 1.53 | —N(CH₃)₂ | 3-OCH₃ | 2 | H | O | |
| 1.54 | C₂H₅ | 3-OCH₃ | 2 | H | O | |
| 1.55 | CF₃ | 3-OCH₃ | 2 | H | O | |
| 1.56 | —OCHF₂ | 3-OCH₃ | 2 | H | O | |
| 1.57 | CH₃ | 2-COOCH₃ | 3 | H | S | |
| 1.58 | OCH₃ | 2-COOCH₃ | 3 | H | S | |
| 1.59 | Cl | 2-COOCH₃ | 3 | H | S | |
| 1.60 | —N(CH₃)₂ | 2-COOCH₃ | 3 | H | S | |
| 1.61 | C₂H₅ | 2-COOCH₃ | 3 | H | S | |
| 1.62 | CF₃ | 2-COOCH₃ | 3 | H | S | |
| 1.63 | —OCHF₂ | 2-COOCH₃ | 3 | H | S | |
| 1.64 | CH₃ | 3-COOCH₃ | 2 | H | S | |
| 1.65 | OCH₃ | 3-COOCH₃ | 2 | H | S | |
| 1.66 | Cl | 3-COOCH₃ | 2 | H | S | |
| 1.67 | —N(CH₃)₂ | 3-COOCH₃ | 2 | H | S | |
| 1.68 | C₂H₅ | 3-COOCH₃ | 2 | H | S | |
| 1.69 | CF₃ | 3-COOCH₃ | 2 | H | S | |
| 1.70 | —OCHF₂ | 3-COOCH₃ | 2 | H | S | |
| 1.71 | CH₃ | 6-F | 2 | H | O | |
| 1.72 | OCH₃ | 6-F | 2 | H | O | |
| 1.73 | Cl | 6-F | 2 | H | O | |
| 1.74 | —N(CH₃)₂ | 6-F | 2 | H | O | |
| 1.75 | C₂H₅ | 6-F | 2 | H | O | |
| 1.76 | CF₃ | 6-F | 2 | H | O | |
| 1.77 | —OCHF₂ | 6-F | 2 | H | O | |
| 1.78 | CH₃ | 6-OCH₃ | 2 | H | O | |
| 1.79 | OCH₃ | 6-OCH₃ | 2 | H | O | |
| 1.80 | Cl | 6-OCH₃ | 2 | H | O | |
| 1.81 | —N(CH₃)₂ | 6-OCH₃ | 2 | H | O | |
| 1.82 | C₂H₅ | 6-OCH₃ | 2 | H | O | |
| 1.83 | CF₃ | 6-OCH₃ | 2 | H | O | |
| 1.84 | —OCHF₂ | 6-OCH₃ | 2 | H | O | |
| 1.85 | CH₃ | 4-Cl | 3 | H | O | 126–128 |
| 1.86 | CH₃ | 2-OCH₃ | 3 | H | O | 148–150 |
| 1.87 | CH₃ | 2-OCH₂CH₂CH₃ | 3 | H | O | |
| 1.88 | OCH₃ | 2-OCH₂CH₂CH₃ | 3 | H | O | |
| 1.89 | CH₃ | 4-COOC₂H₅ | 3 | H | O | |
| 1.90 | OCH₃ | 4-COOC₂H₅ | 3 | H | O | |

TABLE 2

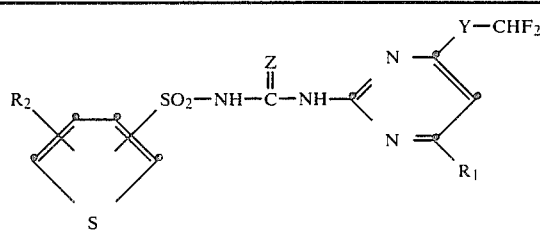

| Compound | R₁ | R₂ | Position of the sulfonyl group | Z | Y | m.p. [°C] |
|---|---|---|---|---|---|---|
| 2.1 | CH₃ | 2-COOCH₃ | 3 | O | O | 178–179 |
| 2.2 | OCH₃ | 2-COOCH₃ | 3 | O | O | 171–174 |
| 2.3 | Cl | 2-COOCH₃ | 3 | O | O | 119–120 |

TABLE 2-continued

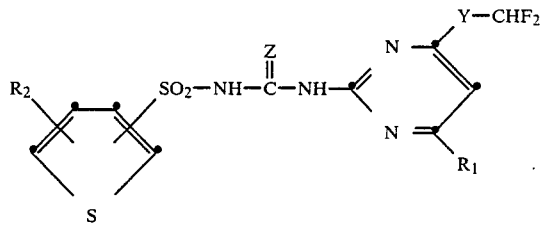

| Compound | R₁ | R₂ | Position of the sulfonyl group | Z | Y | m.p. [°C.] |
|---|---|---|---|---|---|---|
| 2.4 | —N(CH₃)₂ | 2-COOCH₃ | 3 | O | O | 232 |
| 2.5 | C₂H₅ | 2-COOCH₃ | 3 | O | O | |
| 2.6 | CF₃ | 2-COOCH₃ | 3 | O | O | |
| 2.7 | —OCHF₂ | 2-COOCH₃ | 3 | O | O | 198–200 |
| 2.8 | CH₃ | 4-COOCH₃ | 3 | O | O | 159–161 |
| 2.9 | OCH₃ | 4-COOCH₃ | 3 | O | O | 161–162 |
| 2.10 | Cl | 4-COOCH₃ | 3 | O | O | |
| 2.11 | —N(CH₃)₂ | 4-COOCH₃ | 3 | O | O | 225–227 |
| 2.12 | C₂H₅ | 4-COOCH₃ | 3 | O | O | |
| 2.13 | CF₃ | 4-COOCH₃ | 3 | O | O | |
| 2.14 | —OCHF₂ | 4-COOCH₃ | 3 | O | O | 178–179 |
| 2.15 | CH₃ | 2-CO—OCH(CH₃)₂ | 3 | O | O | 186–189 |
| 2.16 | OCH₃ | 2-CO—OCH(CH₃)₂ | 3 | O | O | |
| 2.17 | Cl | 2-CO—OCH(CH₃)₂ | 3 | O | O | |
| 2.18 | —N(CH₃)₂ | 2-CO—OCH(CH₃)₂ | 3 | O | O | |
| 2.19 | OC₂H₅ | 2-CO—OCH(CH₃)₂ | 3 | O | O | |
| 2.20 | CF₃ | 2-CO—OCH(CH₃)₂ | 3 | O | O | |
| 2.21 | —OCHF₂ | 2-CO—OCH(CH₃)₂ | 3 | O | O | |
| 2.22 | CH₃ | 2-CO—OCH₂—CH=CH₂ | 3 | O | O | |
| 2.23 | OCH₃ | 2-CO—OCH₂—CH=CH₂ | 3 | O | O | |
| 2.24 | Cl | 2-CO—OCH₂—CH=CH₂ | 3 | O | O | |
| 2.25 | —N(CH₃)₂ | 2-CO—OCH₂—CH=CH₂ | 3 | O | O | |
| 2.26 | C₂H₅ | 2-CO—OCH₂—CH=CH₂ | 3 | O | O | |
| 2.27 | CF₃ | 2-CO—OCH₂—CH=CH₂ | 3 | O | O | |
| 2.28 | —OCHF₂ | 2-CO—OCH₂—CH=CH₂ | 3 | O | O | |
| 2.29 | CH₃ | 5-Cl | 2 | O | O | |
| 2.30 | OCH₃ | 5-Cl | 2 | O | O | |
| 2.31 | Cl | 5-Cl | 2 | O | O | |
| 2.32 | —N(CH₃)₂ | 5-Cl | 2 | O | O | |
| 2.33 | C₂H₅ | 5-Cl | 2 | O | O | |
| 2.34 | CF₃ | 5-Cl | 2 | O | O | |
| 2.35 | —OCHF₂ | 5-Cl | 2 | O | O | |
| 2.36 | CH₃ | H | 2 | O | O | |
| 2.37 | OCH₃ | H | 2 | O | O | |
| 2.38 | Cl | H | 2 | O | O | |
| 2.39 | —N(CH₃)₂ | H | 2 | O | O | |
| 2.40 | C₂H₅ | H | 2 | O | O | |
| 2.41 | CF₃ | H | 2 | O | O | |
| 2.42 | —OCHF₂ | H | 2 | O | O | |
| 2.43 | CH₃ | H | 3 | O | O | |
| 2.44 | OCH₃ | H | 3 | O | O | |
| 2.45 | Cl | H | 3 | O | O | |
| 2.46 | —N(CH₃)₂ | H | 3 | O | O | |
| 2.47 | C₂H₅ | H | 3 | O | O | |
| 2.48 | CF₃ | H | 3 | O | O | |
| 2.49 | —OCHF₂ | H | 3 | O | O | |
| 2.50 | CH₃ | 2-COOCH₃ | 3 | S | O | |
| 2.51 | OCH₃ | 2-COOCH₃ | 3 | S | O | |
| 2.52 | Cl | 2-COOCH₃ | 3 | S | O | |
| 2.53 | —N(CH₃)₂ | 2-COOCH₃ | 3 | S | O | |
| 2.54 | C₂H₅ | 2-COOCH₃ | 3 | S | O | |
| 2.55 | CF₃ | 2-COOCH₃ | 3 | S | O | |
| 2.56 | —OCHF₂ | 2-COOCH₃ | 3 | S | O | |
| 2.57 | CH₃ | 4-COOCH₃ | 3 | S | O | |
| 2.58 | OCH₃ | 4-COOCH₃ | 3 | S | O | |
| 2.59 | Cl | 4-COOCH₃ | 3 | S | O | |
| 2.60 | —N(CH₃)₂ | 4-COOCH₃ | 3 | S | O | |
| 2.61 | C₂H₅ | 4-COOCH₃ | 3 | S | O | |
| 2.62 | CF₃ | 4-COOCH₃ | 3 | S | O | |
| 2.63 | —OCHF₂ | 4-COOCH₃ | 3 | S | O | |
| 2.64 | CH₃ | 3-COOCH₃ | 2 | S | O | |
| 2.65 | OCH₃ | 3-COOCH₃ | 2 | S | O | |
| 2.66 | Cl | 3-COOCH₃ | 2 | S | O | |
| 2.67 | —N(CH₃)₂ | 3-COOCH₃ | 2 | S | O | |
| 2.68 | C₂H₅ | 3-COOCH₃ | 2 | S | O | |
| 2.69 | CF₃ | 3-COOCH₃ | 2 | S | O | |
| 2.70 | —OCHF₂ | 3-COOCH₃ | 2 | S | O | |
| 2.71 | CH₃ | 3-COOCH₃ | 2 | O | S | |

TABLE 2-continued

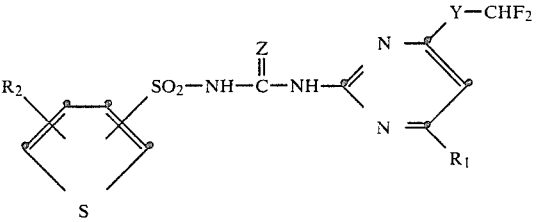

| Compound | R₁ | R₂ | Position of the sulfonyl group | Z | Y | m.p. [°C.] |
|---|---|---|---|---|---|---|
| 2.72 | OCH₃ | 3-COOCH₃ | 2 | O | S | |
| 2.73 | Cl | 3-COOCH₃ | 2 | O | S | |
| 2.74 | —N(CH₃)₂ | 3-COOCH₃ | 2 | O | S | |
| 2.75 | C₂H₅ | 3-COOCH₃ | 2 | O | S | |
| 2.76 | CF₃ | 3-COOCH₃ | 2 | O | S | |
| 2.77 | —OCHF₂ | 3-COOCH₃ | 2 | O | S | |
| 2.78 | CH₃ | 2-COOCH₃ | 3 | O | S | |
| 2.79 | OCH₃ | 2-COOCH₃ | 3 | O | S | |
| 2.80 | Cl | 2-COOCH₃ | 3 | O | S | |
| 2.81 | —N(CH₃)₂ | 2-COOCH₃ | 3 | O | S | |
| 2.82 | C₂H₅ | 2-COOCH₃ | 3 | O | S | |
| 2.83 | CF₃ | 2-COOCH₃ | 3 | O | S | |
| 2.84 | —OCHF₂ | 2-COOCH₃ | 3 | O | S | |
| 2.85 | CH₃ | 4-COOCH₃ | 3 | O | S | |
| 2.86 | OCH₃ | 4-COOCH₃ | 3 | O | S | |
| 2.87 | Cl | 4-COOCH₃ | 3 | O | S | |
| 2.88 | —N(CH₃)₂ | 4-COOCH₃ | 3 | O | S | |
| 2.89 | C₂H₅ | 4-COOCH₃ | 3 | O | S | |
| 2.90 | CF₃ | 4-COOCH₃ | 3 | O | S | |
| 2.91 | —OCHF₂ | 4-COOCH₃ | 3 | O | S | |
| 2.92 | CH₃ | 2-SO₂—CH₃ | 3 | O | O | |
| 2.93 | OCH₃ | 2-SO₂—CH₃ | 3 | O | O | |
| 2.94 | Cl | 2-SO₂—CH₃ | 3 | O | O | |
| 2.95 | —N(CH₃)₂ | 2-SO₂—CH₃ | 3 | O | O | |
| 2.96 | C₂H₅ | 2-SO₂—CH₃ | 3 | O | O | |
| 2.97 | CF₃ | 2-SO₂—CH₃ | 3 | O | O | |
| 2.98 | —OCHF₂ | 2-SO₂—CH₃ | 3 | O | O | |
| 2.99 | CH₃ | 3-SO₂—CH₃ | 2 | O | O | |
| 2.100 | OCH₃ | 3-SO₂—CH₃ | 2 | O | O | |
| 2.101 | Cl | 3-SO₂—CH₃ | 2 | O | O | |
| 2.102 | —N(CH₃)₂ | 3-SO₂—CH₃ | 2 | O | O | |
| 2.103 | C₂H₅ | 3-SO₂—CH₃ | 2 | O | O | |
| 2.104 | CF₃ | 3-SO₂—CH₃ | 2 | O | O | |
| 2.105 | —OCHF₂ | 3-SO₂—CH₃ | 2 | O | O | |
| 2.106 | CH₃ | 4-SO₂—CH₃ | 3 | O | O | |
| 2.107 | OCH₃ | 4-SO₂—CH₃ | 3 | O | O | |
| 2.108 | Cl | 4-SO₂—CH₃ | 3 | O | O | |
| 2.109 | —N(CH₃)₂ | 4-SO₂—CH₃ | 3 | O | O | |
| 2.110 | C₂H₅ | 4-SO₂—CH₃ | 3 | O | O | |
| 2.111 | CF₃ | 4-SO₂—CH₃ | 3 | O | O | |
| 2.112 | —OCHF₂ | 4-SO₂—CH₃ | 3 | O | O | |
| 2.113 | CH₃ | 2-SO₂—N(CH₃)₂ | 3 | O | O | |
| 2.114 | OCH₃ | 2-SO₂—N(CH₃)₂ | 3 | O | O | |
| 2.115 | Cl | 2-SO₂—N(CH₃)₂ | 3 | O | O | |
| 2.116 | —N(CH₃)₂ | 2-SO₂—N(CH₃)₂ | 3 | O | O | |
| 2.117 | C₂H₅ | 2-SO₂—N(CH₃)₂ | 3 | O | O | |
| 2.118 | CF₃ | 2-SO₂—N(CH₃)₂ | 3 | O | O | |
| 2.119 | —OCHF₂ | 2-SO₂—N(CH₃)₂ | 3 | O | O | |
| 2.120 | CH₃ | 4-SO₂—N(CH₃)₂ | 3 | O | O | |
| 2.121 | OCH₃ | 4-SO₂—N(CH₃)₂ | 3 | O | O | |
| 2.122 | Cl | 4-SO₂—N(CH₃)₂ | 3 | O | O | |
| 2.123 | —N(CH₃)₂ | 4-SO₂—N(CH₃)₂ | 3 | O | O | |
| 2.124 | C₂H₅ | 4-SO₂—N(CH₃)₂ | 3 | O | O | |
| 2.125 | CF₃ | 4-SO₂—N(CH₃)₂ | 3 | O | O | |
| 2.126 | —OCHF₂ | 4-SO₂—N(CH₃)₂ | 3 | O | O | |
| 2.127 | CH₃ | 3-SO₂—N(CH₃)₂ | 2 | O | O | |
| 2.128 | OCH₃ | 3-SO₂—N(CH₃)₂ | 2 | O | O | |
| 2.129 | Cl | 3-SO₂—N(CH₃)₂ | 2 | O | O | |
| 2.130 | —N(CH₃)₂ | 3-SO₂—N(CH₃)₂ | 2 | O | O | |
| 2.131 | C₂H₅ | 3-SO₂—N(CH₃)₂ | 2 | O | O | |
| 2.132 | CF₃ | 3-SO₂—N(CH₃)₂ | 2 | O | O | |
| 2.133 | —OCHF₂ | 3-SO₂—N(CH₃)₂ | 2 | O | O | |
| 2.134 | CH₃ | 2-CO—CH₃ | 3 | O | O | |
| 2.135 | OCH₃ | 2-CO—CH₃ | 3 | O | O | |
| 2.136 | Cl | 2-CO—CH₃ | 3 | O | O | |
| 2.137 | —N(CH₃)₂ | 2-CO—CH₃ | 3 | O | O | |
| 2.138 | C₂H₅ | 2-CO—CH₃ | 3 | O | O | |
| 2.139 | CF₃ | 2-CO—CH₃ | 3 | O | O | |

TABLE 2-continued

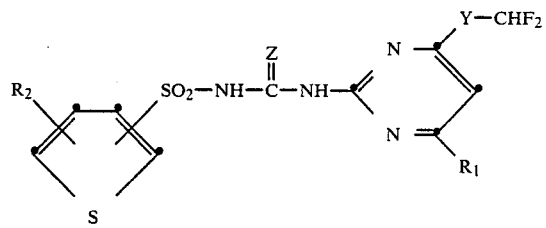

| Compound | $R_1$ | $R_2$ | Position of the sulfonyl group | Z | Y | m.p. [°C.] |
|---|---|---|---|---|---|---|
| 2.140 | —OCHF$_2$ | 2-CO—CH$_3$ | 3 | O | O | |
| 2.141 | CH$_3$ | 2-COOC$_2$H$_5$ | 3 | O | O | |
| 2.142 | OCH$_3$ | 2-COOC$_2$H$_5$ | 3 | O | O | |
| 2.143 | Cl | 2-COOC$_2$H$_5$ | 3 | O | O | |
| 2.144 | —N(CH$_3$)$_2$ | 2-COOC$_2$H$_5$ | 3 | O | O | |
| 2.145 | C$_2$H$_5$ | 2-COOC$_2$H$_5$ | 3 | O | O | |
| 2.146 | CF$_3$ | 2-COOC$_2$H$_5$ | 3 | O | O | |
| 2.147 | —OCHF$_2$ | 2-COOC$_2$H$_5$ | 3 | O | O | |
| 2.148 | CH$_3$ | 2-CO—OCH$_2$—C≡CH | 3 | O | O | 182–186 |
| 2.149 | OCH$_3$ | 2-CO—OCH$_2$—C≡CH | 3 | O | O | |
| 2.150 | Cl | 2-CO—OCH$_2$—C≡CH | 3 | O | O | |
| 2.151 | —N(CH$_3$)$_2$ | 2-CO—OCH$_2$—C≡CH | 3 | O | O | |
| 2.152 | C$_2$H$_5$ | 2-CO—OCH$_2$—C≡CH | 3 | O | O | |
| 2.153 | CF$_3$ | 2-CO—OCH$_2$—C≡CH | 3 | O | O | |
| 2.154 | —OCHF$_2$ | 2-CO—OCH$_2$—C≡CH | 3 | O | O | |
| 2.155 | CH$_3$ | 3-COOCH$_3$ | 2 | O | O | |
| 2.156 | OCH$_3$ | 3-COOCH$_3$ | 2 | O | O | |
| 2.157 | Cl | 3-COOCH$_3$ | 2 | O | O | |
| 2.158 | —N(CH$_3$)$_2$ | 3-COOCH$_3$ | 2 | O | O | |
| 2.159 | C$_2$H$_5$ | 3-COOCH$_3$ | 2 | O | O | |
| 2.160 | CF$_3$ | 3-COOCH$_3$ | 2 | O | O | |
| 2.161 | —OCHF$_2$ | 3-COOCH$_3$ | 2 | O | O | |
| 2.162 | CH$_3$ | 3-COOC$_2$H$_5$ | 2 | O | O | |
| 2.163 | OCH$_3$ | 3-COOC$_2$H$_5$ | 2 | O | O | |
| 2.164 | Cl | 3-COOC$_2$H$_5$ | 2 | O | O | |
| 2.165 | —N(CH$_3$)$_2$ | 3-COOC$_2$H$_5$ | 2 | O | O | |
| 2.166 | C$_2$H$_5$ | 3-COOC$_2$H$_5$ | 2 | O | O | |
| 2.167 | CF$_3$ | 3-COOC$_2$H$_5$ | 2 | O | O | |
| 2.168 | —OCHF$_2$ | 3-COOC$_2$H$_5$ | 2 | O | O | |
| 2.169 | CH$_3$ | 3-CO—OCH(CH$_3$)$_2$ | 2 | O | O | |
| 2.170 | OCH$_3$ | 3-CO—OCH(CH$_3$)$_2$ | 2 | O | O | |
| 2.171 | Cl | 3-CO—OCH(CH$_3$)$_2$ | 2 | O | O | |
| 2.172 | —N(CH$_3$)$_2$ | 3-CO—OCH(CH$_3$)$_2$ | 2 | O | O | |
| 2.173 | C$_2$H$_5$ | 3-CO—OCH(CH$_3$)$_2$ | 2 | O | O | |
| 2.174 | CF$_3$ | 3-CO—OCH(CH$_3$)$_2$ | 2 | O | O | |
| 2.175 | —OCHF$_2$ | 3-CO—OCH(CH$_3$)$_2$ | 2 | O | O | |
| 2.176 | CH$_3$ | 3-CO—N(CH$_3$)$_2$ | 2 | O | O | |
| 2.177 | OCH$_3$ | 3-CO—N(CH$_3$)$_2$ | 2 | O | O | |
| 2.178 | Cl | 3-CO—N(CH$_3$)$_2$ | 2 | O | O | |
| 2.179 | —N(CH$_3$)$_2$ | 3-CO—N(CH$_3$)$_2$ | 2 | O | O | |
| 2.180 | C$_2$H$_5$ | 3-CO—N(CH$_3$)$_2$ | 2 | O | O | |
| 2.181 | CF$_3$ | 3-CO—N(CH$_3$)$_2$ | 2 | O | O | |
| 2.182 | —OCHF$_2$ | 3-CO—N(CH$_3$)$_2$ | 2 | O | O | |
| 2.183 | CH$_3$ | 2-CO—N(CH$_3$)$_2$ | 3 | O | O | |
| 2.184 | OCH$_3$ | 2-CO—N(CH$_3$)$_2$ | 3 | O | O | |
| 2.185 | Cl | 2-CO—N(CH$_3$)$_2$ | 3 | O | O | |
| 2.186 | —N(CH$_3$)$_2$ | 2-CO—N(CH$_3$)$_2$ | 3 | O | O | |
| 2.187 | C$_2$H$_5$ | 2-CO—N(CH$_3$)$_2$ | 3 | O | O | |
| 2.188 | CF$_3$ | 2-CO—N(CH$_3$)$_2$ | 3 | O | O | |
| 2.189 | —OCHF$_2$ | 2-CO—N(CH$_3$)$_2$ | 3 | O | O | |
| 2.190 | CH$_3$ | 4-CO—N(CH$_3$)$_2$ | 3 | O | O | |
| 2.191 | OCH$_3$ | 4-CO—N(CH$_3$)$_2$ | 3 | O | O | |
| 2.192 | Cl | 4-CO—N(CH$_3$)$_2$ | 3 | O | O | |
| 2.193 | —N(CH$_3$)$_2$ | 4-CO—N(CH$_3$)$_2$ | 3 | O | O | |
| 2.194 | C$_2$H$_5$ | 4-CO—N(CH$_3$)$_2$ | 3 | O | O | |
| 2.195 | CF$_3$ | 4-CO—N(CH$_3$)$_2$ | 3 | O | O | |
| 2.196 | —OCHF$_2$ | 4-CO—N(CH$_3$)$_2$ | 3 | O | O | |
| 2.197 | CH$_3$ | 2-NO$_2$ | 3 | O | O | |
| 2.198 | OCH$_3$ | 2-NO$_2$ | 3 | O | O | |
| 2.199 | OCHF$_2$ | 2-NO$_2$ | 3 | O | O | |
| 2.200 | CH$_3$ | 3-NO$_2$ | 2 | O | O | |
| 2.201 | OCH$_3$ | 3-NO$_2$ | 2 | O | O | |
| 2.202 | OCHF$_2$ | 3-NO$_2$ | 2 | O | O | |
| 2.203 | CH$_3$ | 3-NO$_2$ | 4 | O | O | |
| 2.204 | OCH$_3$ | 3-NO$_2$ | 4 | O | O | |
| 2.205 | OCHF$_2$ | 3-NO$_2$ | 4 | O | O | |
| 2.206 | CH$_3$ | 4-COO—CH$_2$—C≡CH | 3 | O | O | |
| 2.207 | OCH$_3$ | 4-COO—CH$_2$—C≡CH | 3 | O | O | |

TABLE 2-continued

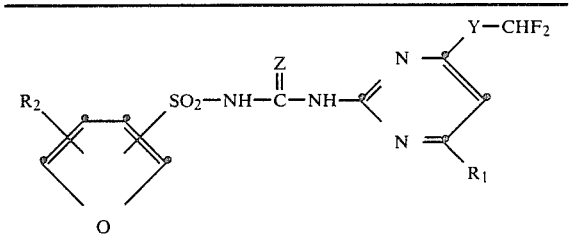

| Compound | R₁ | R₂ | Position of the sulfonyl group | Z | Y | m.p. [°C.] |
|---|---|---|---|---|---|---|
| 2.208 | OCH₃ | 4-COO—CH₂—CH=CH₂ | 3 | O | O | |
| 2.209 | CH₃ | 4-COOC₂H₅ | 3 | O | O | |
| 2.210 | OCH₃ | 4-COOC₂H₅ | 3 | O | O | |

TABLE 3

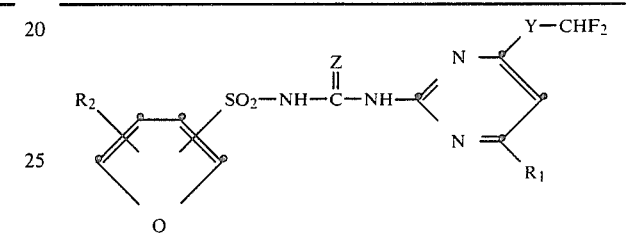

| Compound | R₁ | R₂ | Position of the sulfonyl group | Z | Y | m.p. [°C.] |
|---|---|---|---|---|---|---|
| 3.1 | CH₃ | 2-COOCH₃ | 3 | O | O | |
| 3.2 | OCH₃ | 2-COOCH₃ | 3 | O | O | |
| 3.3 | Cl | 2-COOCH₃ | 3 | O | O | |
| 3.4 | —N(CH₃)₂ | 2-COOCH₃ | 3 | O | O | |
| 3.5 | C₂H₅ | 2-COOCH₃ | 3 | O | O | |
| 3.6 | CF₃ | 2-COOCH₃ | 3 | O | O | |
| 3.7 | —OCHF₂ | 2-COOCH₃ | 3 | O | O | |
| 3.8 | CH₃ | 3-COOCH₃ | 2 | O | O | |
| 3.9 | OCH₃ | 3-COOCH₃ | 2 | O | O | |
| 3.10 | Cl | 3-COOCH₃ | 2 | O | O | |
| 3.11 | —N(CH₃)₂ | 3-COOCH₃ | 2 | O | O | |
| 3.12 | C₂H₅ | 3-COOCH₃ | 2 | O | O | |
| 3.13 | CF₃ | 3-COOCH₃ | 2 | O | O | |
| 3.14 | —OCHF₂ | 3-COOCH₃ | 2 | O | O | |
| 3.15 | CH₃ | 4-COOCH₃ | 3 | O | O | |
| 3.16 | OCH₃ | 4-COOCH₃ | 3 | O | O | |
| 3.17 | Cl | 4-COOCH₃ | 3 | O | O | |
| 3.18 | —N(CH₃)₂ | 4-COOCH₃ | 3 | O | O | |
| 3.19 | C₂H₅ | 4-COOCH₃ | 3 | O | O | |
| 3.20 | CF₃ | 4-COOCH₃ | 3 | O | O | |
| 3.21 | —OCHF₂ | 4-COOCH₃ | 3 | O | O | |
| 3.22 | CH₃ | 2-COOCH₃ | 3 | S | O | |
| 3.23 | OCH₃ | 2-COOCH₃ | 3 | S | O | |
| 3.24 | Cl | 2-COOCH₃ | 3 | S | O | |
| 3.25 | —N(CH₃)₂ | 2-COOCH₃ | 3 | S | O | |
| 3.26 | C₂H₅ | 2-COOCH₃ | 3 | S | O | |
| 3.27 | CF₃ | 2-COOCH₃ | 3 | S | O | |
| 3.28 | —OCH₂ | 2-COOCH₃ | 3 | S | O | |

TABLE 4

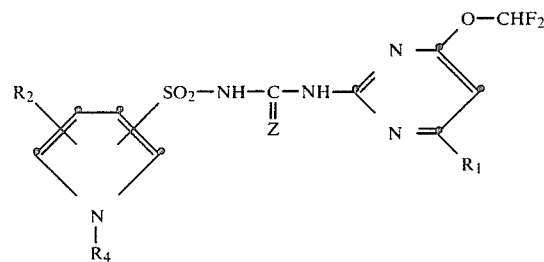

| Compound | R₁ | R₂ | Position of the sulfonyl group | R₄ | Z | m.p. [°C.] |
|---|---|---|---|---|---|---|
| 4.1 | CH₃ | H | 2 | H | O | 189 |
| 4.2 | OCH₃ | H | 2 | H | O | |
| 4.3 | Cl | H | 2 | H | O | |
| 4.4 | —N(CH₃)₂ | H | 2 | H | O | |
| 4.5 | C₂H₅ | H | 2 | H | O | |
| 4.6 | CF₃ | H | 2 | H | O | |
| 4.7 | OCHF₂ | H | 2 | H | O | |
| 4.8 | CH₃ | H | 3 | H | O | 173–174 |
| 4.9 | OCH₃ | H | 3 | H | O | |
| 4.10 | Cl | H | 3 | H | O | |
| 4.11 | —N(CH₃)₂ | H | 3 | H | O | |
| 4.12 | C₂H₅ | H | 3 | H | O | |
| 4.13 | CF₃ | H | 3 | H | O | |

TABLE 4-continued

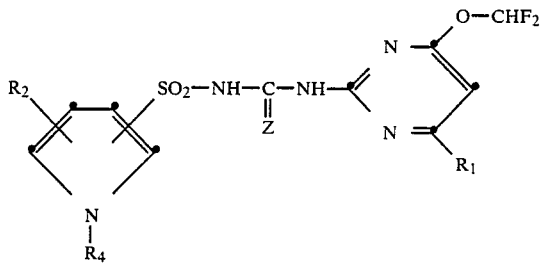

| Compound | R₁ | R₂ | Position of the sulfonyl group | R₄ | Z | m.p. [°C.] |
|---|---|---|---|---|---|---|
| 4.14 | —OCHF₂ | H | 3 | H | O | |
| 4.15 | CH₃ | H | 3 | CH₃ | O | |
| 4.16 | OCH₃ | H | 3 | CH₃ | O | |
| 4.17 | Cl | H | 3 | CH₃ | O | |
| 4.18 | —N(CH₃)₂ | H | 3 | CH₃ | O | |
| 4.19 | C₂H₅ | H | 3 | CH₃ | O | |
| 4.20 | CF₃ | H | 3 | CH₃ | O | |
| 4.21 | —OCHF₂ | H | 3 | CH₃ | O | |
| 4.22 | CH₃ | H | 2 | —(CH₂)₂—CN | O | |
| 4.23 | OCH₃ | H | 2 | —(CH₂)₂—CN | O | |
| 4.24 | Cl | H | 2 | —(CH₂)₂—CN | O | |
| 4.25 | —N(CH₃)₂ | H | 2 | —(CH₂)₂—CN | O | |
| 4.26 | C₂H₅ | H | 2 | —(CH₂)₂—CN | O | |
| 4.27 | CF₃ | H | 2 | —(CH₂)₂—CN | O | |
| 4.28 | —OCHF₂ | H | 2 | —(CH₂)₂—CN | O | |
| 4.29 | CH₃ | H | 2 | CH₃ | O | |
| 4.30 | OCH₃ | H | 2 | CH₃ | O | |
| 4.31 | Cl | H | 2 | CH₃ | O | |
| 4.32 | N(CH₃)₂ | H | 2 | CH₃ | O | |
| 4.33 | CH₂CH₃ | H | 2 | CH₃ | O | |
| 4.34 | CF₃ | H | 2 | CH₃ | O | |
| 4.35 | OCHF₂ | H | 2 | CH₃ | O | |
| 4.36 | CH₃ | H | 3 | CH₃ | O | |
| 4.37 | OCH₃ | H | 3 | CH₃ | O | |
| 4.38 | Cl | H | 3 | CH₃ | O | |
| 4.39 | N(CH₃)₂ | H | 3 | CH₃ | O | |
| 4.40 | CH₂CH₃ | H | 3 | CH₃ | O | |
| 4.41 | CF₃ | H | 3 | CH₃ | O | |
| 4.42 | OCHF₂ | H | 3 | CH₃ | O | |
| 4.43 | CH₃ | H | 3 | CH₃ | S | |
| 4.44 | OCH₃ | H | 3 | CH₃ | S | |
| 4.45 | Cl | H | 3 | CH₃ | S | |
| 4.46 | N(CH₃)₂ | H | 3 | CH₃ | S | |
| 4.47 | CH₂CH₃ | H | 3 | CH₃ | S | |
| 4.48 | CF₃ | H | 3 | CH₃ | S | |
| 4.49 | OCHF₂ | H | 3 | CH₃ | S | |
| 4.50 | CH₃ | 3-COOCH₃ | 2 | CH₃ | O | |
| 4.51 | OCH₃ | 3-COOCH₃ | 2 | CH₃ | O | |
| 4.52 | Cl | 3-COOCH₃ | 2 | CH₃ | O | |
| 4.53 | N(CH₃)₂ | 3-COOCH₃ | 2 | CH₃ | O | |
| 4.54 | CH₂CH₃ | 3-COOCH₃ | 2 | CH₃ | O | |
| 4.55 | CF₃ | 3-COOCH₃ | 2 | CH₃ | O | |
| 4.56 | OCHF₂ | 3-COOCH₃ | 2 | CH₃ | O | |

EXAMPLE 5

Formulation examples for compounds of formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4-5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silocone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

BIOLOGICAL EXAMPLES

EXAMPLE 6

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 lux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the action on the plants is assessed according to the following rating:

1: plants have not emerged or are totally withered
2-3: very pronounced action
4-6: medium action
7-8: weak action
9: no action (as untreated controls).

Preemergence action:
Concentration of the test compound emulsion: 70.8 ppm

| Compound | Test plant | | | |
|---|---|---|---|---|
| | Nasturtium | Stellaria | Agrostis | Digitaria |
| 1.15 | 1 | 1 | 1 | 1 |
| 1.29 | 2 | 3 | 2 | 3 |
| 1.50 | 1 | 2 | 1 | 1 |
| 1.86 | 2 | 6 | 2 | 2 |
| 2.1 | 1 | 1 | 1 | 1 |
| 2.2 | 1 | 1 | 1 | 1 |
| 2.3 | 2 | 4 | 2 | 3 |
| 2.4 | 1 | 4 | 1 | 3 |
| 2.7 | 1 | 3 | 1 | 6 |
| 2.8 | 1 | 2 | 1 | 2 |
| 2.9 | 1 | 2 | 1 | 2 |
| 2.11 | 1 | 2 | 1 | 2 |
| 2.14 | 1 | 2 | 1 | 3 |

(b) In a greenhouse, plant seeds are sown in flower pots of 12-13 cm diameter. Immediately after sowing, the surface of the soil is treated with an aqueous dispersion or solution of the compounds to be tested. Concentrations of 125 and 30 g of a.i./ha are employed. The pots are then kept in the greenhouse at 22°-25° C. and 50-70% relative humidity. The test is evaluated 3 weeks later in accordance with the rating indicated above.

| | Preemergence action | | | | | | | |
|---|---|---|---|---|---|---|---|---|
| | Action | | | | | | | |
| | Compound 2.2 | | Compound 2.8 | | Compound 2.9 | | Compound 2.14 | |
| | Rate of application in g % a.i./ha | | | | | | | |
| Test plant | 125 | 30 | 125 | 30 | 125 | 30 | 125 | 30 |
| barley | 8 | 9 | 2 | 4 | 2 | 6 | 7 | 9 |
| wheat | 6 | 8 | 3 | 4 | 3 | 7 | 8 | 9 |

-continued

| | Preemergence action | | | | | | | |
|---|---|---|---|---|---|---|---|---|
| | Action | | | | | | | |
| | Compound 2.2 | | Compound 2.8 | | Compound 2.9 | | Compound 2.14 | |
| | Rate of application in g % a.i./ha | | | | | | | |
| Test plant | 125 | 30 | 125 | 30 | 125 | 30 | 125 | 30 |
| maize | 6 | 8 | 7 | 8 | 8 | 9 | 9 | 9 |
| dry rice | 3 | 6 | 1 | 1 | 1 | 2 | 6 | 7 |
| Alopecurus myos. | 5 | 6 | 2 | 3 | 1 | 2 | 2 | 4 |
| Echinochloa c.g. | 8 | 9 | 3 | 4 | 4 | 7 | 9 | 9 |
| Rottboellia ex. | 8 | 9 | 6 | 7 | 5 | 7 | 6 | 9 |
| Cyperus escul. | 4 | 8 | 1 | 4 | 1 | 2 | 3 | 9 |
| soybeans | 8 | 8 | 8 | 9 | 5 | 7 | 7 | 9 |
| cotton | 4 | 7 | 4 | 5 | 3 | 5 | 9 | 9 |
| sugar beet | 2 | 2 | 2 | 3 | 1 | 1 | 2 | 4 |
| Abutilon | 2 | 4 | 5 | 6 | 2 | 4 | 7 | 7 |
| Xanthium Sp. | 7 | 9 | 4 | 5 | 3 | 4 | 6 | 9 |
| Amaranthus ret. | 3 | 3 | 2 | 3 | 2 | 2 | 2 | 2 |
| Chenopodium Sp. | 4 | 6 | 5 | 6 | 2 | 2 | 3 | 9 |
| Solanum nigrum | 5 | 8 | 3 | 4 | 2 | 3 | 3 | 9 |
| Ipomoea | 4 | 9 | 6 | 8 | 4 | 6 | 3 | 9 |
| Sinapis | 2 | 3 | 3 | 4 | 1 | 1 | 3 | 9 |
| Stellaria | 3 | 4 | 3 | 4 | 2 | 2 | 2 | 2 |
| Chrysanthe. leuc. | 2 | 3 | 2 | 2 | 1 | 1 | 2 | 9 |
| Galium aparine | 3 | 5 | 3 | 3 | 1 | 2 | 2 | 5 |
| Viola tricolor | 2 | 2 | 3 | 3 | 1 | 2 | 3 | 9 |
| Veronica Sp. | 1 | 2 | 1 | 1 | 1 | 1 | 2 | 2 |

EXAMPLE 7

Postermergence herbicidal action (contact action)

A number of weeds and cultivated plants, both monocots and dicots, are sprayed postemergence, in the 4- to 6-leaf stage, with an aqueous dispersion of test compound at rates of application of 125 and 30 g of a.i./ha, and then kept at 24°-26° and 45-60% relative humidity. The test is evaluated 15 days after treatment using the same rating as in the preemergence test.

| | Postemergence action | | | |
|---|---|---|---|---|
| | Action | | | |
| | Compound 2.2 | | Compound 2.9 | |
| | Rate of application in g of a.i./ha | | | |
| Test plant | 125 | 30 | 125 | 30 |
| wheat | 8 | 9 | 7 | 8 |
| maize | 8 | 9 | 8 | 9 |
| dry rice | 8 | 9 | 5 | 7 |
| Alopecurus myos. | 6 | 7 | 4 | 7 |
| Echinochloa c.g. | 8 | 9 | 6 | 7 |
| Cyperus escul. | 4 | 6 | 3 | 4 |
| soybeans | 6 | 7 | 5 | 7 |
| cotton | 5 | 6 | 8 | 8 |
| sugar beet | 2 | 2 | 2 | 2 |
| Abutilon | 3 | 4 | 2 | 3 |
| Xanthium Sp. | 2 | 2 | 2 | 2 |
| Chenopodium Sp. | 5 | 6 | 3 | 5 |
| Ipomoea | 4 | 7 | 4 | 5 |
| Sinapis | 2 | 2 | 3 | 3 |
| Galium aparine | 4 | 5 | 4 | 6 |
| Viola tricolor | 2 | 3 | 2 | 4 |

EXAMPLE 8

Growth inhibition of tropical cover crops

The test plants (*centrosema plumieri* and *centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

What is claimed is:

1. A compound selected from the group consisting of a sulfonylurea of the formula:

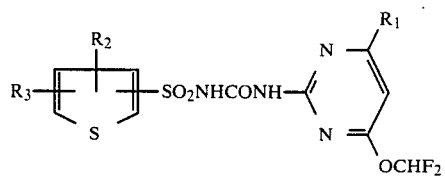

wherein
R$_1$ is halo, alkyl of 1 to 4 carbon atoms, alkoxy of 1 to 4 carbon atoms, haloalkyl of 1 to 4 carbon atoms, haloalkoxy of 1 to 4 carbon atoms, or dialkylamino, each alkyl of which has from 1 to 4 carbon atoms;

R$_2$ is hydrogen, halo, alkyl of 1 to 3 carbon atoms, alkoxy of 1 to 3 carbon atoms, alkylsulfonyl of 1 to 3 carbon atoms, N,N-dialkylaminosulfonyl each alkyl of which has from 1 to 3 carbon atoms, alkanoyl of 1 to 4 carbon atoms, alkoxycarbonyl of 1 to 4 carbon atoms, allyloxycarbonyl, 2-methoxyethoxycarbonyl or propargyloxycarbonyl; and R$_3$ is hydrogen, halo, alkyl of 1 to 3 carbon atoms, methoxy, nitro or trifluoromethyl; and the salts thereof.

2. A compound according to claim 1 wherein R$_3$ is hydrogen and R$_2$ is hydrogen, fluoro, chloro, alkoxy of 1 to 3 carbon atoms, acetyl, nitro, methylsulfonyl, allyloxycarbonyl, 2-methoxyethoxycarbonyl, propargyloxycarbonyl, dimethylaminosulfonyl, or alkoxycarbonyl of 1 to 4 carbon atoms.

3. A compound according to claim 2 wherein R$_1$ is chloro, methyl, ethyl, methoxy, ethoxy, fluoromethyl, trifluoromethyl, difluoromethoxy or dimethylamino.

4. A compound according to claim 3 wherein R$_2$ is vicinal to the depicted sulfonyl group.

5. A compound according to claim 4 wherein R$_2$ is alkoxycarbonyl of 1 to 4 carbon atoms.

6. A compound selected from the group consisting of a sulfonylurea of the formula:

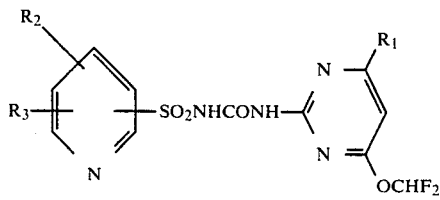

wherein
R$_1$ is halo, alkyl of 1 to 4 carbon atoms, alkoxy of 1 to 4 carbon atoms, haloalkyl of 1 to 4 carbon atoms, haloalkoxy of 1 to 4 carbon atoms, or dialkylamino, each alkyl of which has from 1 to 4 carbon atoms;

$R_2$ is hydrogen, halo, alkyl of 1 to 3 carbon atoms, alkoxy of 1 to 3 carbon atoms, alkylsulfonyl of 1 to 3 carbon atoms, N,N-dialkylaminosulfonyl each alkyl of which has from 1 to 3 carbon atoms, alkanoyl of 1 to 4 carbon atoms, alkoxycarbonyl of 1 to 4 carbon atoms, allyloxycarbonyl, 2-methoxyethoxycarbonyl or propargyloxycarbonyl; and $R_3$ is hydrogen, halo, alkyl of 1 to 3 carbon atoms, methoxy, nitro or trifluoromethyl; and the salts thereof.

7. A compound according to claim 6 wherein $R_3$ is hydrogen and $R_2$ is hydrogen, fluoro, chloro, alkoxy of 1 to 3 carbon atoms, acetyl, nitro, methylsulfonyl, allyloxycarbonyl, 2-methoxyethoxycarbonyl, propargyloxycarbonyl, dimethylaminosulfonyl, or alkoxycarbonyl of 1 to 4 carbon atoms.

8. A compound according to claim 7 wherein $R_1$ is chloro, methyl, ethyl, methoxy, ethoxy, fluoromethyl, trifluoromethyl, difluoromethoxy or dimethylamino.

9. A compound according to claim 8 wherein $R_2$ is vicinal to the depicted sulfonyl group.

10. The method of controlling the growth of weeds in desirable crops which comprises applying to the weeds or to their environs an effective amount of a compound according to claim 1.

11. A herbicidal composition comprising an effective amount of a compound according to claim 1 in combination with an inert carrier.

12. The method of controlling the growth of weeds in desirable crops which comprises applying to the weeds or to their environs an effective amount of a compound according to claim 6.

13. A herbicidal composition comprising an effective amount of a compound according to claim 6 in combination with an inert carrier.

14. N-(2-Methoxycarbonyl-3-thienylsulfonyl)-N'-(4-difluoromethoxy-6-methylpyrimidin-2-yl)urea according to claim 1.

15. N-(4-Methoxycarbonyl-3-thienylsulfonyl)-N'-(4-difluoromethoxy-6-methylpyrimidin-2-yl)urea according to claim 1.

16. N-(2-Chloro-3-pyridinylsulfonyl)-N'-(4-difluoromethoxy-6-methylpyrimidin-2-yl)urea according to claim 6.

17. N-(4-Methoxycarbonyl-3-thienylsulfonyl)-N'-(4-difluoromethoxy-6-methoxypyrimidin-2-yl)urea according to claim 1.

* * * * *